(12) United States Patent
Fricker et al.

(10) Patent No.: US 6,329,207 B1
(45) Date of Patent: Dec. 11, 2001

(54) WET CHEMICAL INDICATOR FOR THE EVALUATION OF PERACETIC ACID CHEMISTRIES

(75) Inventors: Christopher M. Fricker, Concord; Brian C. Wojcieck, Willoughby; Paul D. Walkley, Jr., Parma, all of OH (US); Robert F. Korb, Durham, NC (US); Giridhar Shamsunder, Raleigh, NC (US); Elijah L. Booker, Jr., Durham, NC (US); Kathleen A. Hughes, Raleigh, NC (US); Lewis I. Schwartz, Bratenahl, OH (US)

(73) Assignee: Steris Corporation, Mentor, OH (US)

( * ) Notice: Subject to any disclaimer, the term of this patent is extended or adjusted under 35 U.S.C. 154(b) by 0 days.

(21) Appl. No.: 09/249,587

(22) Filed: Feb. 11, 1999

(51) Int. Cl.$^7$ .................................................. A61L 2/28
(52) U.S. Cl. ....................... 436/129; 436/164; 422/28; 422/58
(58) Field of Search .................. 422/28, 58; 436/164, 436/165, 1, 129

(56) References Cited

U.S. PATENT DOCUMENTS

| | | |
|---|---|---|
| 4,459,936 * | 7/1984 | Karle .................................. 116/207 |
| 4,732,850 | 3/1988 | Brown et al. ........................... 435/31 |
| 5,518,927 * | 5/1996 | Malchesky et al. ..................... 436/1 |
| 5,620,656 * | 4/1997 | Wensky et al. ......................... 422/28 |
| 5,662,808 * | 9/1997 | Blaney et al. ........................ 210/749 |
| 5,736,355 * | 4/1998 | Dyke et al. ............................ 435/31 |
| 5,770,393 | 6/1998 | Dalmasso et al. ..................... 435/31 |
| 5,834,313 * | 11/1998 | Lin ............................................ 436/1 |
| 5,866,356 * | 2/1999 | Albert et al. ........................... 435/31 |
| 5,942,438 * | 8/1999 | Autonoplos et al. .................... 436/1 |
| 5,989,852 * | 11/1999 | Hendricks et al. ..................... 435/31 |
| 6,096,270 * | 8/2000 | Rapkin et al. .......................... 422/61 |

\* cited by examiner

*Primary Examiner*—Jill Warden
*Assistant Examiner*—LaToya I. Cross
(74) *Attorney, Agent, or Firm*—Fay, Sharpe, Fagan, Minnich & McKee, LLP

(57) ABSTRACT

A wet chemical indicator for peracetic acid solutions includes an indicator for peracetic acid and an inhibitor. The inhibitor is selected to inhibit a selected peracetic acid concentration in a reproducible sample of a solution containing peracetic acid. The indicator exhibits an observable change when the selected concentration of peracetic acid is exceeded. In this manner, a rapid indication of whether the peracetic acid solution is of a required minimum strength is provided.

22 Claims, 1 Drawing Sheet

WET CHEMICAL INDICATOR FOR THE EVALUATION OF PERACETIC ACID CHEMISTRIES

BACKGROUND OF THE INVENTION

The present invention relates to the sterilization and disinfection arts. It finds particular application in conjunction with the evaluation of peracetic acid sterilization or disinfection baths and will be described with particular reference thereto. It should be appreciated, however, that the invention is also applicable to other liquid sterilization and disinfection processes where the sterilant or disinfectant is effective above a minimum effective concentration, such as liquid hydrogen peroxide or sodium hypochlorite sterilization or disinfection systems.

Peracetic acid is a useful disinfectant and sterilant for a variety of applications including disinfection of waste and sterilization of medical equipment, packaging containers, and the like. Peracetic acid has the ability to be reused over a period of time, allowing instruments to be repeatedly sterilized or disinfected throughout the day in the same bath.

In use, peracetic precursors are mixed with water and other chemicals in a bath and the items to be sterilized or disinfected are immersed in the bath. Decontaminated items are then typically rinsed before use. To ensure effective sterilization or disinfection within a preselected period of time, the concentration of the peracetic acid is maintained above a minimum effective level, typically around 2300 parts per million for sterilization of medical instruments. For disinfection, peracetic acid concentrations of 5 ppm and above are used. For peracetic acid concentrations of at or above the minimum effective level, complete sterilization or disinfection is expected. Because the peracetic acid tends to decompose over time, it is important to evaluate the bath periodically to determine whether the minimum effective level of peracetic acid is present.

Currently, it is often assumed that the bath will be at or above the minimum effective concentration for a period of around eight hours where a selected initial concentration of peracetic acid is present in the bath. However, differences in ambient temperature, the quantity of items to be disinfected or sterilized and the level of contamination on the items can lead to considerable variation in the useful life of the bath. In addition, storage conditions sometimes lead to degradation of peracetic acid precursors before use. For medical instruments in particular, therefore, a more accurate method of evaluating the peracetic acid is required. Dippable chemically-treated papers are easy to use but lack accuracy, particularly at concentrations suitable for sterilizing and disinfecting. Although chemical titration methods provide an accurate measure of the concentration of peracetic acid in a solution, these methods are time-consuming and open to possible operator errors. Premeasured vials of titrating solution have been utilized to detect low and trace concentrations of peracetic acid, e.g., residual peracetic acid after sterilizing and rinsing. Manually measuring a unit volume of solution into the vial raises the specter of human error.

The present invention provides a new and improved wet chemical indicator for the evaluation of peracetic acid solutions which overcomes the above-referenced problems and others.

SUMMARY OF THE INVENTION

In accordance with one aspect of the present invention, a wet chemical system is provided for evaluating peracetic acid solutions. An indicator for peracetic acid and an inhibitor for inhibiting a selected concentration of peracetic acid in a sample quantity of a peracetic solution are disposed within a container. The inhibitor prevents the indicator from detecting peracetic acid at concentrations below the selected concentration.

In accordance with another aspect of the present invention, a method is provided for evaluating a peracetic acid sterilizing or disinfecting solution. An indicator for peracetic acid and an inhibitor for inhibiting a selected concentration of peracetic acid in a sample of a sterilizing or disinfecting solution are combined with the sample of the sterilizing or disinfecting solution to be tested. The combination of indicator, inhibitor, and peracetic acid sterilizing or disinfecting solution are observed for a change in a measurable property. The change indicates that the concentration of peracetic acid in the sterilizing or disinfecting solution exceeds the selected concentration.

One advantage of the present invention is that it provides a rapid and inexpensive method of determining the adequacy of a peracetic acid solution for sterilizing or disinfecting instruments.

Another advantage of the present invention is that it provides a clear yes-or-no indication of whether a minimum effective concentration of peracetic acid is present.

Another advantage of the present invention is that it permits efficient use of a peracetic acid sterilizing or disinfecting solution.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
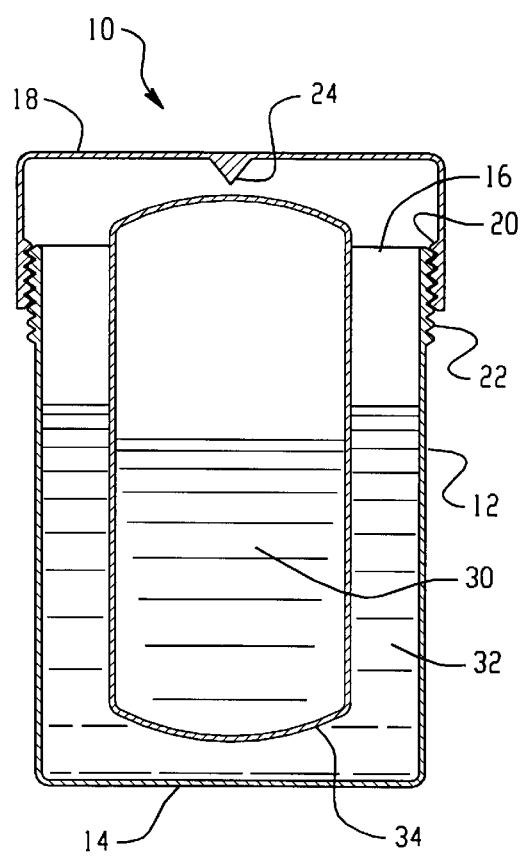
FIG. 1 is a cross section of a wet chemical indicator for the evaluation of peracetic acid of the present invention; and, FIG. 2 is a cross section of an alternative embodiment of a wet chemical indicator for the evaluation of peracetic acid of the present invention.

With reference to FIG. 1, a container 10 includes an approximately cylindrical transparent side 12 and a base 14, sealed to the side. The side defines an opening 16. A removable cap 18, seals the opening 16. The cap 18 preferably has a screw fitting 20 capable of engaging a similar fitting 22 on the side 12 of the container 10. Alternatively, the cap 18 has a press-fit seal that engages the side 12 of the container 10.

A calorimetrically oxidizable species, or indicator 30 and a inhibitor 32 are disposed within the container 10. The inhibitor inhibits a selected concentration of peracetic acid, usually selected to be the minimum effective level for sterilization or disinfection. A measured quantity of a peracetic acid sterilizing or disinfecting solution to be tested is added to the container 10, the cap 18 positioned to seal the opening 16 and the mixture shaken for a short period, typically less than ten seconds. A change in a property of the solution, such as a color change, indicates that the concentration of peracetic acid in the sterilizing or disinfecting solution is at or above the minimum effective level for sterilization or disinfection.

The indicator 30 is preferably one which exhibits a visible color change when mixed with peracetic acid, such as starch-iodide solution, n,n diethyl-p-phenylene diamine (DPD), ferroin indicator, ferrous thiocyanate or cerric sulphate. Starch-iodide is a particularly preferred indicator because of its long shelf life and because it exhibits a distinct color change (colorless to blue-black) in the presence of concentrations of peracetic acid. Typical contaminants found on medical instruments do not interfere with the detection of peracetic acid by the starch-iodide indicator at the contaminant concentration levels to be expected in sterilization or disinfection baths. A starch-iodide solution is readily prepared by mixing approximately equal parts of a starch solution and a potassium or (sodium) iodide solution. The ratio is not critical, however, the starch component serving only to emphasize the color change caused by the conversion of potassium iodide to iodine in the presence of peracetic acid. A suitable solution contains 0.05–1.0% by weight of starch and 0.05–1.0% by weight potassium or sodium iodide.

Another preferred indicator is DPD. This indicator is preferably used in combination with a halogen phosphate buffer (HPB). It is particularly useful in solutions containing chlorine because it is unaffected by the chlorine. However, the color change is not as distinct as with starch-iodine. In the presence of peracetic acid, the color of the solution changes from clear to a light pink, then to a dark pink as the concentration of peracetic acid increases. For accurate results, it is preferable to employ a spectrophotometer or a set of standard solutions of appropriate colors to evaluate the color change when the peracetic acid concentration is close to the selected minimum effective level.

The inhibitor 32 is a chemical which inhibits a known concentration of peracetic acid, preventing the indicator 30 from detecting peracetic acid below that concentration. For example, when the desired peracetic acid concentration (the trip point) is 2500 ppm, the inhibitor 32 dose is adjusted to inhibit 2500 ppm of peracetic acid. The indicator 30 then only detects the uninhibited peracetic acid in excess of that amount. The combination of the inhibitor 32 with the indicator 30 thus creates an easy to read yes-or-no indicator for peracetic acid sterilization and disinfection solutions. Absence of a color change indicates that the peracetic acid solution needs to be replenished, while a distinct color change indicates that the solution can be safely used for further sterilization or disinfection of instruments.

Preferred inorganic inhibitors 32 are sodium thiosulfate and salts of heavy metals including ferrous salts, copper salts and cobalt salts. Preferred organic inhibitors 32 include hydroquinone and derivatives, t-butyl catechol, ethanolamines, and phenols. A particularly preferred indicator 30 and inhibitor 32 combination is starch-iodide solution with sodium thiosulfate because the mixture is stable over fairly long periods of time, allowing the two chemicals to be stored together in the container 10. Sodium thiosulfate is also an effective inhibitor for DPD.

By adjusting the concentration of the inhibitor 32, different preselected concentrations of peracetic acid can be detected. Since the indicator 30 detects concentrations of as low as a few parts per million peracetic acid, peracetic acid solutions in the range of about 10 ppm to about 10,000 ppm are measurable. TABLE 1 gives examples of indicator and inhibitor concentration ranges suitable for testing peracetic acid solutions.

TABLE 1

Test Solutions for mixing with an equal quantity of a peracetic acid solution to generate a distinct color change at 2500 ppm peracetic acid.

| FORMULA 1 | |
|---|---|
| Indicator | 0.4% Sodium Iodide |
| | 0.2% Starch |
| Inhibitor | 0.01N Sodium Thiosulfate |
| FORMULA 2 | |
| Indicator | 0.4% Sodium Iodide |
| | 0.2% Starch |
| Inhibitor | 0.02N Sodium Thiosulfate |
| FORMULA 3 | |
| Indicator | 0.4% Sodium Iodide |
| | 0.2% Starch |
| Inhibitor | 0.1N Cerric Ammonium Sulfate in 1.0N Sulphuric Acid |
| FORMULA 4 | |
| Indicator | 0.4% Sodium Iodide |
| Inhibitor | 0.02N Sodium Thiosulfate |
| FORMULA 5 | |
| Indicator | 0.5–2.5 g/l n,n Diethyl-p-Phenylene-Diamine (DPD) |
| Buffer | Halogen Phosphate Buffer |
| Inhibitor | 0.01N Sodium Thiosulfate |

Thus, for example, to make 100 ml of FORMULA 1, one would mix about 10.0 ml of 0.1 normal solution of sodium thiosulfate with 0.2 grams of starch and 0.4 grams of sodium iodide. Deionized water is added to 100 ml.

The exact quantity of the inhibitor used varies according to the desired peracetic acid trip point. TABLE 2 shows how the trip point varies with the quantity of inhibitor for a HPD/DPD/sodium thiosulfate indicator/inhibitor system. In each test, a peracetic acid solution of known concentration (established by conventional titration methods) was mixed with a 0.1N thiosulfate solution in HPB. 1000 ml of a solution of 2.5 g/l DPD was then added. Color changes were observed by eye after about five seconds.

TABLE 2 records the average color change of one to four tests as a number between 0 and 4, 0 indicating no color change, 4 indicating a change to dark pink. The results show that as the quantity of the inhibitor (sodium thiosulfate) is increased, the trip point shifts towards a higher peracetic acid concentration. For example, if a trip point color of 3 is selected, the peracetic acid concentration at the trip point shifts from 2400 ppm at 1400 μL of inhibitor to 2600 ppm at 2000–2100 μL of inhibitor and 2700 ppm at 2200 μL of inhibitor. Thus, the trip point is readily adjusted by varying the quantity of inhibitor. Sharper trip points would be obtained if the tests were evaluated with a spectrophotometer or standard color solutions.

TABLE 2

| Inhibitor | Peracetic Acid Concentration (ppm.) | | | | | |
|---|---|---|---|---|---|---|
| Volume μL | >2700 | >2600 | >2500 | >2400 | >2300 | >2200 |
| 1400 | 3 | 3 | 3 | 3 | 2 | 0.5 |
| 2000 | | 3 | 2 | | 1.5 | |
| 2100 | 3 | 3 | 1.5 | 2 | 2 | |
| 2200 | 3 | 2 | 1.5 | | 1.5 | 2 |

Where the indicator 30 and inhibitor 32 are unstable in combination, the indicator and inhibitor are preferably separately contained. For FORMULA 5, for example, the halogen phosphate buffer is conveniently combined with the inhibitor and is preferably kept separate from the indicator (DPD) until used for testing a sample of a peracetic acid solution. Optionally, a sealed frangible inner container 34, such as a glass ampule, holding the indicator 30, is disposed within the container 10. After the peracetic acid has been added to the container 10, the inner container 34 is broken, releasing the indicator 30 into the inhibitor-peracetic acid solution. Alternatively, the inner container 34 is broken immediately prior to addition of the peracetic acid solution. Preferably the container 10 is constructed from a flexible material such as polypropylene, allowing the inner container 34 to be broken by squeezing the side 12 of the container. Alternatively, a downward motion on the cap 18, causes a dart 24 to fracture the inner container 34.

Optionally, the indicator 30 and or the inhibitor 32 are solids which readily dissolve in and interact with the peracetic acid solution.

The measured quantity of peracetic acid solution is preferably obtained by drawing the solution into a calibrated eyedropper or syringe. Alternatively, a swab, capable of absorbing a known volume of peracetic acid solution, is dipped into the solution. The swab and absorbed peracetic acid solution are then introduced to the container 10. A particularly preferred method of introducing a reproducible quantity of peracetic acid to the container 10 is by drawing the peracetic acid directly into the container under vacuum as shown in FIG. 2.

Figure 2:
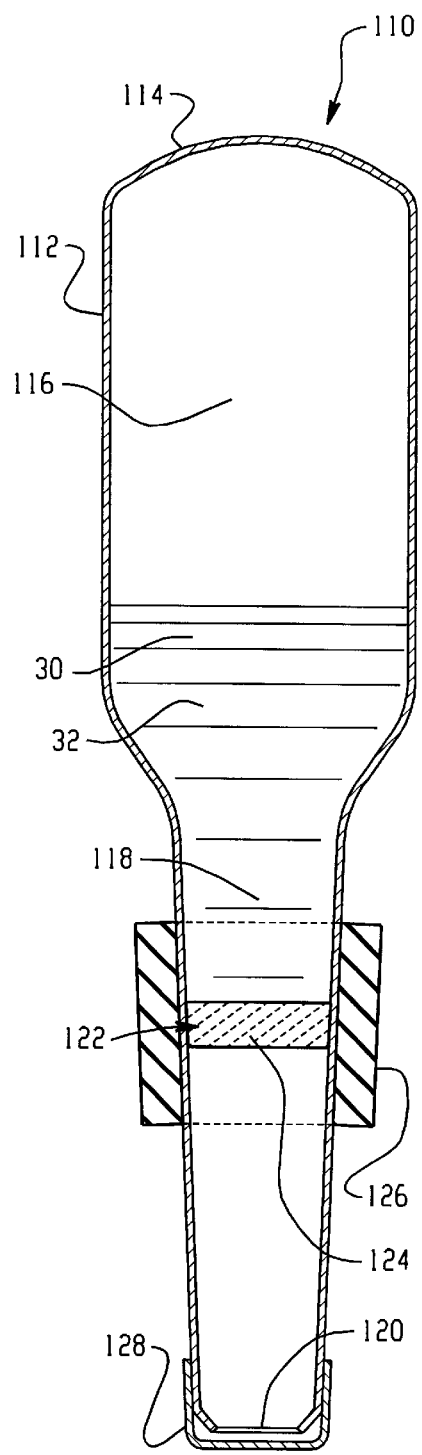

With reference to FIG. 2, an alternative embodiment includes a container 110 with a base 114 and a side 112, sealed to the base. The side tapers inwards, thereby defining an open area 116 adjacent to the base 114 and a narrow tube 118, extending from the open area. The end of the tube 118 furthest from the base 114 defines an opening 120. The container 110 is preferably constructed from a transparent rigid material, such as glass, capable of maintaining a vacuum within the open area 116. The tube includes a frangible area 122.

Measured quantities of an indicator 30 and an inhibitor 32 are disposed in the container 110 under vacuum. A frangible seal 124 is formed within the tube 118 to block the tube. This prevents the indicator 30 and inhibitor 32 from leaking from the container 110 during storage.

Where the container 110 is constructed of glass, the seal 124 is preferably formed by fusing an area of the tube at a high temperature. A sleeve 126 tightly surrounds the area 122 of the tube 118 containing the seal 124. The sleeve 126 is preferably constructed of a flexible material, such as silicon rubber, such that the seal 124 may be broken by bending the tube 118 within the area 122 under the sleeve 126. The seal 124 is broken by breaking the area 122 of the tube 118. The sleeve 126 maintains the integrity of the tube 118 by sealing around the broken area and prevents shards of glass from escaping.

The wet chemical indicator is preferably assembled for use by drawing the required quantities of indicator 30 and inhibitor 32 into the container 110 through the tube 118 into the open area 116, then drawing a vacuum in the container 110, sealing the tube 118 with seal 124, and surrounding the sealed area 122 of the tube with the flexible sleeve 126.

A sample of the peracetic acid solution to be tested is drawn into the container 110 by first inserting the tube 118 into the solution, then breaking the seal 124. The vacuum in the container 110 draws a reproducible quantity of the solution into the container to mix with the indicator 30 and inhibitor 32. The container 110 is inverted and shaken to mix the three components together. When peracetic acid is present in the solution at concentrations above the minimum effective concentration, a color change is rapidly visible through the side 112 of the container 110. Thus, an accurate determination of whether sufficient peracetic acid is present in the sterilizing or disinfecting solution is obtained within a few seconds.

Optionally, a cap 128 is attached to the opening 120 after drawing the peracetic acid to seal the opening and prevent leakage from the container 110. The cap also limits the entry of oxygen into the tube, which is beneficial to the accuracy of some indicator/inhibitor systems.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A wet chemical test system for evaluating peracetic acid solutions, the wet chemical system comprising:
   a) a container including an opening;
   b) an indicator for peracetic acid, disposed within the container, the indicator being selected from the group consisting of diethyl phenylene diamine (DPD), ferroin indicator, ferrous thiocyanate and cerric sulphate; and,
   c) an inhibitor disposed within the container, for inhibiting a selected concentration of peracetic acid in a reproducible quantity of a peracetic acid solution, the inhibitor preventing the indicator from detecting peracetic acid at concentrations below the selected concentration.

2. The wet chemical system of claim 1, wherein the inhibitor is selected from a group comprising sodium thiosulfate, salts of heavy metals including ferrous salts, copper salts and cobalt salts, hydroquinone and derivatives, t-butyl catechol, ethanolamines, and phenols.

3. The wet chemical system of claim 1, further comprising a measure for obtaining a selected quantity of a peracetic acid solution.

4. The wet chemical system of claim 3, wherein the measure for obtaining the measured quantity of a peracetic acid solution is one of an eyedropper, syringe, and swab.

5. A wet chemical test system for evaluating a peracetic acid sterilant solution, the wet chemical system comprising:
   a) a container including an opening;
   b) an indicator for peracetic acid, disposed within the container;
   c) an inhibitor disposed within the container, for inhibiting a selected concentration of peracetic acid in a reproducible quantity of a sterilant solution, the inhibitor preventing the indicator from detecting peracetic acid at concentrations below the selected concentration, the container including a cap for covering the opening; and
   d) an inner, frangible compartment, disposed within the container, for separately enclosing one of the indicator and the inhibitor, the cap including a dart for opening the inner compartment, a movement of the cap from a first position to a second position causing the dart to puncture the inner compartment, thereby allowing the indicator and the inhibitor to mix.

6. The wet chemical system of claim 5, wherein the container includes sides constructed of a flexible material such that the inner compartment is broken when the sides are squeezed or bent.

7. The wet chemical system of claim 5, wherein the indicator is selected from the group consisting of starch-iodide solution, diethyl phenylene diamine (DPD), ferroin indicator, ferrous thiocyanate and cerric sulphate.

8. A chemical test formulation for determining whether a concentration of peracetic acid in a solution exceeds a selected concentration by about 10 ppm or more, the chemical formulation comprising:
  a) an indicator for peracetic acid, disposed within a container; and
  b) an inhibitor for inhibiting the selected concentration of peracetic acid in a reproducible quantity of a peracetic acid solution, the inhibitor preventing the indicator from detecting peracetic acid at concentrations below the selected concentration, the indicator exhibiting a visible color change when mixed with the inhibitor and a selected quantity of peracetic acid solution in which the concentration of the peracetic acid exceeds the selected concentration by about 10 ppm or more, the inhibitor being disposed in the container.

9. The chemical formulation of claim 8, wherein the indicator includes sodium iodide and starch and wherein the inhibitor includes sodium thiosulfate.

10. A chemical test formulation for determining when a concentration of peracetic acid in a solution exceeds a selected concentration, the chemical formulation comprising:
  a) an indicator for peracetic acid, the indicator including 0.4% sodium iodide and 0.2% starch; and
  b) an inhibitor for inhibiting the selected concentration of peracetic acid in a reproducible quantity of a peracetic acid solution, the inhibitor preventing the indicator from detecting peracetic acid at concentrations below the selected concentration of peracetic acid, the inhibitor including 0.01–0.02N sodium thiosulfate solution.

11. A wet chemical test system for evaluating peracetic acid solutions, the wet chemical system comprising:
  a) a container;
  b) an indicator for peracetic acid which includes diethyl phenylene diamine, disposed within the container;
  c) an inhibitor disposed within the container, for inhibiting a selected concentration of peracetic acid in a reproducible quantity of a peracetic acid solution, the inhibitor including sodium thiosulfate, the inhibitor preventing the indicator from detecting peracetic acid at concentrations below the selected concentration; and
  (d) a halogen phosphate buffer.

12. The wet chemical test system of claim 11, wherein:
  the indicator includes diethyl phenylene diamine at a concentration of about 0.5–2.5 g/l; and
  the inhibitor includes 0.01N sodium thiosulfate.

13. A wet chemical system for evaluating a sterilant solution, the wet chemical system comprising:
  a) a container including an opening, a frangible seal sealing the opening in the container, the container being at a selected sub-atmospheric pressure such that breaking the seal while the opening is immersed in a solution causes a fixed quantity of the solution to be drawn into the container;
  b) an indicator for the sterilant, disposed within the container; and
  c) an inhibitor disposed within the container, for inhibiting a selected concentration of the sterilant in a reproducible quantity of a sterilant solution, the inhibitor preventing the indicator from detecting the sterilant at concentrations below the selected concentration.

14. The wet chemical system of claim 13, wherein the container defines an open area and a tube connected to the open area, the tube defining the opening to the container, the tube including the frangible seal, such that breaking the seal while the opening is immersed in a solution including peracetic acid causes a fixed amount of the solution to be drawn into the container through the tube.

15. The wet chemical system of claim 14, wherein the tube includes a frangible area adjacent to the seal, the wet chemical system further comprising a flexible sleeve, the sleeve surrounding the frangible area, such that a solution including peracetic acid is drawn into the container without leaking from the tube when the frangible area of the tube is broken while the opening is immersed in the solution.

16. A method for evaluating a peracetic acid sterilizing or disinfecting solution, the method comprising:
  a) taking an indicator for peracetic acid and an inhibitor, the inhibitor selected to inhibit a selected concentration of peracetic acid in a sample of a sterilizing or disinfecting solution;
  b) combining the indicator and the inhibitor with a sample of a sterilizing or disinfecting solution to be tested
  c) monitoring the combination of the indicator, inhibitor, and peracetic acid sterilizing solution for a color change, the color change indicating that the concentration of peracetic acid in the sterilizing or disinfecting solution exceeds the selected concentration.

17. The method of claim 16, further comprising:
  obtaining the sample of peracetic acid solution by drawing the solution into a partially evacuated container, the container holding the indicator and the inhibitor.

18. The method of claim 17, further comprising:
  drawing a vacuum in the container through an opening in the container;
  sealing the opening in the container with a frangible seal;
  partially immersing the container in the peracetic acid solution such that the opening in the container is submerged; and,
  breaking the frangible seal to allow peracetic acid to be drawn through the opening and into the container.

19. The method of claim 16, wherein the selected concentration of peracetic acid is the concentration required for effective sterilization or disinfection of instruments.

20. A method for evaluating a peracetic acid sterilizing or disinfecting solution, the method comprising:
  a) separately disposing an indicator for peracetic acid in a frangible container;
  b) combining the indicator and an inhibitor with a sample of a sterilizing or disinfecting solution to be tested by breaking the frangible container to allow the indicator to mix with the peracetic acid solution and the inhibitor, the inhibitor selected to inhibit a selected concentration of peracetic acid in a sample of a sterilizing or disinfecting solution;
  c) monitoring the combination of the indicator, inhibitor, and peracetic acid sterilizing solution for a change in a spectrophotometrically or visually detectable property, the change indicating that the concentration of peracetic acid in the sterilizing or disinfecting solution exceeds the selected concentration.

21. A method for evaluating a peracetic acid sterilizing or disinfecting solution, the method comprising:

a) taking an indicator for peracetic acid and an inhibitor, the inhibitor selected to inhibit a selected concentration of peracetic acid in a sample of a sterilizing or disinfecting solution, the selected concentration being about 2300–2500 ppm;

b) combining the indicator and the inhibitor with a sample of a sterilizing or disinfecting solution to be tested;

c) monitoring the combination of the indicator, inhibitor, and peracetic acid sterilizing solution for a change in a spectrophotometrically or visually detectable property, the change indicating that the concentration of peracetic acid in the sterilizing or disinfecting solution exceeds the selected concentration.

22. In a wet chemical system for evaluating peracetic acid solutions including an indicator for peracetic acid, the improvement comprising:

the wet chemical system including an inhibitor in a sufficient amount for inhibiting a selected threshold concentration of peracetic acid, such that only peracetic acid present in excess of the threshold concentration interacts with the indicator, a detectable change in a chemical or physical property of the indicator resulting only when the system is exposed to a sample of a solution which includes a concentration of peracetic acid in excess of the threshold concentration.

* * * * *